United States Patent [19]

Zimmermann et al.

[11] Patent Number: 5,319,111

[45] Date of Patent: Jun. 7, 1994

[54] PREPARATION OF TETRAHYDROFURAN AND GAMMA-BUTYROLACTONE

[75] Inventors: Horst Zimmermann, Mannheim; Karl Brenner, Ludwigshafen; Hans-Juergen Scheiper, Mutterstadt; Wolfgang Sauer, Kirchheimbolanden; Horst Hartmann, Boehl-Iggelheim, all of Fed. Rep. of Germany

[73] Assignee: BASF Aktiengesellschaft, Ludwigshafen, Fed. Rep. of Germany

[21] Appl. No.: 931,117

[22] Filed: Aug. 17, 1992

Related U.S. Application Data

[63] Continuation of Ser. No. 658,086, Feb. 20, 1991, abandoned.

Foreign Application Priority Data

Feb. 20, 1990 [DE] Fed. Rep. of Germany ....... 4004293

[51] Int. Cl.$^5$ .................. C07D 307/08; C07D 307/33
[52] U.S. Cl. .................................. 549/325; 549/326; 549/508; 549/509
[58] Field of Search ................ 549/325, 326, 508, 509

[56] References Cited

U.S. PATENT DOCUMENTS

| | | | |
|---|---|---|---|
| 4,093,633 | 6/1978 | Tanabe et al. | 260/346.11 |
| 4,096,156 | 6/1978 | Freudenberger et al. | 260/343.6 |
| 4,155,919 | 5/1979 | Ramioulle et al. | 260/346.11 |
| 4,588,827 | 5/1986 | Mueller et al. | 549/509 |
| 4,751,334 | 6/1988 | Turner et al. | 568/864 |
| 4,851,085 | 7/1989 | De Thomas | 549/295 |
| 4,912,236 | 3/1990 | Palm et al. | 549/509 |
| 4,940,805 | 7/1990 | Fischer et al. | 549/326 |

FOREIGN PATENT DOCUMENTS 1293151 10/1972 United Kingdom .
1320839 6/1973 United Kingdom .

*Primary Examiner*—C. Warren Ivy
*Assistant Examiner*—Ba K. Trinh
*Attorney, Agent, or Firm*—John H. Shurtleff

[57] ABSTRACT

A process for the preparation of tetrahydrofuran or tetrahydrofuran and γ-butyrolactone from the product of the hydrogenation of maleic acid, succinic acid, maleic anhydride, succinic anhydride and/or fumaric acid, by treating the crude hydrogenation product, without prior work-up, at from 100° to 300° C. with a protic acid, and isolating pure tetrahydrofuran and γ-butyrolactone from the resultant reaction mixture by distillation.

10 Claims, No Drawings

PREPARATION OF TETRAHYDROFURAN AND GAMMA-BUTYROLACTONE

This application is a continuation of application Ser. No. 658,086, filed Feb. 20, 1991 now abandoned.

The present invention relates to a process for the preparation of tetrahydrofuran or tetrahydrofuran and γ-butyrolactone from the product of the hydrogenation of maleic acid, succinic acid, maleic anhydride, succinic anhydride and/or fumaric acid.

The following abbreviations are used below: MA=maleic acid, SA=succinic acid, MAA=maleic anhydride, SAA=succinic anhydride, THF=tetrahydrofuran, GBL=γ-butyrolactone, BD=1,4-butanediol and FA=fumaric acid.

The acid-catalyzed cyclization of BD to give THF has been disclosed, for example, in DE-A 34 32 575 and DE-A 29 30 144.

The hydrogenation of said starting materials to give mixtures of THF, GBL and/or BD has been disclosed, for example, in U.S. Pat. No. 4,155,919, U.S. Pat. No. 4,096,156, DE-A 21 33 768, EP-A-184 055, U.S. Pat. No. 4,940,805 and U.S. Pat. No. 4,751,334. THF, GBL and BD are obtained as the principal products in various ratios, depending on the catalyst used and on the hydrogenation conditions. In addition, a large number of byproducts, for example dibutylene glycol, 4-hydroxybutyrates, 4-hydroxybutyl butyrate, 4-hydroxybutyl succinate, butoxybutanol, etc., are formed.

The hydrogenation mixtures obtained by this process are worked up by distillation. Due to the by-products obtained in the hydrogenation product, this work-up method is difficult and requires high apparative complexity and energy consumption. This is particularly true if pure THF or GBL is desired. BD in hydrogenation products must be separated from THF and GBL and possibly from other products before it can be converted into THF by cyclization.

Thus, U.S. Pat. No. 4,751,334 describes a process for the hydrogenation of maleic acid esters which gives a product essentially comprising THF, GBL and BD. Distillative work-up of the hydrogenation mixture gives a low-boiling component comprising THF, alcohols and low-boiling impurities at the head of the column, while the bottom product is split into a GBL/diethyl succinate azeotrope and crude butanediol in further distillation columns. The useful products THF, GBL and BD in the particular fractions are still very impure and must subsequently be worked up again in separate distillation units. After separation from THF and GBL, the BD can, if desired, be dehydrated by this process in a further cyclization step to give THF.

U.S. Pat. No. 4,851,085 describes a process for removing discoloring impurities from GBL, in which the GBL is treated with an acid. A prerequisite for the success of this process is to use GBL in a purity of 95% or more.

As a consequence of the high cost of separating, isolating and purifying the useful products THF, GBL and BD, the processes for the preparation of THF and GBL by hydrogenating maleic acid and derivatives thereof are uneconomic. It is an object of the present invention to develop a process which allows the economical preparation and isolation of THF and GBL from the product of the hydrogenation of maleic acid and which, in particular, allows pure THF and GBL to be prepared and isolated at considerably reduced purification cost.

We have found that this object is achieved by a process for the preparation of THF or THF and γ-butyrolactone from the product of the hydrogenation of maleic acid, succinic acid, maleic anhydride, succinic anhydride and/or fumaric acid, which comprises treating the crude hydrogenation product, without prior work-up, at from 100 to 300° C. with a protic acid, and isolating pure tetrahydrofuran and γ-butyrolactone from the resultant reaction mixture by distillation.

For the purposes of the present invention, the term hydrogenation product is taken to mean the products, containing BD or BD and THF or BD, THF and GBL as valuable constituents, of the catalytic hydrogenation of MA, SA, FA, MAA and/or SAA.

Using the process according to the invention, namely the acid treatment of the hydrogenation products, the BD in the hydrogenation products is surprisingly converted virtually quantitatively into THF, and the by-products of the hydrogenation are converted into THF or GBL with acid catalysis. The byproducts which cannot be converted into THF or GBL surprisingly decompose under the acid-treatment conditions to give products which do not interfere with the distillative work-up of the valuable products THF and GBL, so that THF, for example as THF/water azeotrope, and GBL can be obtained simply in a particularly pure form. The THF/water azeotrope produced can be split into its constituents THF and water by standard methods, for example by the process of U.S. Pat. No. 4,912,236.

A wide range of protic acids can be used for the novel acid-treatment of the hydrogenation products; for example, conventional inorganic protic acids, such as hydrochloric acid, sulfuric acid, phosphoric acid or tetrafluoroboric acid, and organic protic acids, such as oxalic acid, p-toluenesulfonic acid or methanesulfonic acid, can be used. Virtually any protic acid which is sufficiently acidic to catalyze the dehydration of BD and which does not have an oxidizing effect under the reaction conditions can be used. Thus, the process according to the invention can also use, for example, heteropolyacids, such as tungstophosphoric acids, tungstosilicic acids or molybdatophosphoric acids.

In addition to the abovementioned conventional protic acids, it is also possible to use solids which are acidic and act as Brönstedt acids, for example dehydrating, acidic oxides of aluminum, magnesium, titanium and zirconium, aluminum phosphates, zeolites, such as faujasites, pentasils or silicalites, and phyllosilicates, such as montmorillonites, bleaching earths, such as bentonites, fuller's earths, etc. It is of course also possible to use organic cation exchangers, for example sulfonated phenol-formaldehyde resins, sulfonated styrene-divinylbenzene copolymers, polyacrylates, cation exchangers based on cellulose or sulfonated charcoals as acidic catalyst.

Preference is given to sulfuric acid, phosphoric acid and phyllosilicates, in particular bentonite and organic cation exchangers. Particular preference is given to sulfuric acid.

The acid treatment is generally carried out by adding from 0.01 to 10% by weight, preferably from 0.01 to 5% by weight, particularly preferably from 0.1 to 1% by weight, of the particular acid to the hydrogenation products. The protic acid can be added as an aqueous solution or, if the particular acid allows, in gas form, eg. hydrogen chloride, or in solid form, eg. p-toluenesulfonic acid, bentonite or tungstophosphoric acid. Liquid protic acids, for example sulfuric acid or phosphoric acid, are generally used in the form of their commercially available, concentrated solutions, but it is also possible, in correspondingly higher amounts, to use dilute solutions of these acids. It is of course still necessary for the dilute solutions of these acids to be sufficiently acidic to effectively catalyze the cyclization of BD to give THF. However, preference is given to concentrated acids.

The acid treatment is generally carried out at from 100 to 300° C. The final reaction temperature which should advantageously be established also depends on the type of acid used and can in each case be determined by means of a few preliminary experiments. For example, the acid treatment with sulfuric acid is advantageously carried out at from 100 to 150° C., in particular at from 110 to 130° C., whereas the reaction temperatures are preferably from 150 to 200° C., in particular from 170 to 190° C., when bentonite is used and are generally advantageously from 250 to 300° C. in the case of treatment with phosphoric acid.

The acid treatment can be carried out either under atmospheric pressure or under superatmospheric pressure, preferably under the inherent pressure of the reaction system. Since the particular hydrogenation products in most cases already contain relatively large amounts of THF, it is possible, at the same time as the acid treatment, to remove the low-boiling components of the reaction mixture, comprising a THF/water azeotrope, by distillation. In the initial stages of the distillation, it is primarily the THF already present in the hydrogenation products which is stripped off, while the proportion of tetrahydrofuran newly formed from BD increases in the distillate as the treatment continues. Since the THF already present in the hydrogenation products is virtually inert under the acid-treatment conditions, removal of the tetrahydrofuran from the hydrogenation products by distillation before the acid treatment thereof should be regarded as equivalent to removing the tetrahydrofuran during the acid treatment.

The acid treatment of the hydrogenation products can be carried out batchwise in stirred reactors, which are pressure-stable if necessary, or continuously, for example in stirred reactor cascades. Solid cyclization catalysts, for example bleaching earths, can be suspended in the reaction medium, but preference is given to a fixed bed arrangement of a catalyst through which the particular hydrogenation products are passed, using the pool or trickle procedure.

Since both the THF already present in the hydrogenation products and that newly formed can be removed continuously from the reaction mixture by distillation during the acid treatment, a non-volatile residue, essentially comprising GBL and even less volatile compounds, from which GBL can easily be removed by distillation and obtained in a purity of greater than 99%, remains in the reaction apparatus at the end of the acid treatment. The catalyst acid remains in the distillation residue and can be regenerated if desired. The process according to the invention thus facilitates successive isolation of high-purity THF and GBL from the hydrogenation of MAA in one and the same plant.

The hydrogenation processes do not comprise the subject-matter of the present invention. In the process according to the invention, the hydrogenation products from any process for hydrogenating MA, MAA, SA, SAA or FA, in particular the products of the above-mentioned hydrogenation processes, can be employed.

Since the products from the various hydrogenation processes have different compositions, THF and GBL are of course produced in different proportions on treatment according to the invention of the various hydrogenation products. For example, virtually only THF is obtained according to the invention from the products of the process of U.S. Pat. No. 4,155,919, while considerable amounts of GBL can be obtained according to the invention in addition to THF from the products of the process of U.S. Pat. No. 4,940,805 Preference is given in the process according to the invention to products obtained by hydrogenating melts of MA, MAA, SA, SAA or FA.

The GBL obtained by the process according to the invention and the THF obtained according to the invention by splitting the THF/water azeotrope are so pure that they can be used without further purification for the vast majority of applications.

THF and GBL are important solvents and are also used as intermediates in the preparation of poly-THF (polytetramethylene glycol) and N-methylpyrrolidone.

EXAMPLES

Example 1

A typical product of the hydrogenation of MAA, having the composition as shown in Table 1, was treated with 0.1% by weight of concentrated sulphuric acid and heated at 130° C. for several hours. During this time, the THF already present and water were removed from the reaction mixture by distillation as a THF/water azeotrope together with the THF and water newly formed during the reaction. After complete cyclization of the butanediol and decomposition of the byproducts, the temperature was reduced to 110° C., the pressure to 10 mbar, and GBL was distilled off. The GBL obtained in this way had a purity of greater than 99%. The distillation residue was not worked up further and was discarded. The THF/water azeotrope was split into its two constituents by the method of DE-A 37 26 805, giving THF having a purity of greater than 99.95%.

Table 2 shows the product distribution after acid treatment of the hydrogenation products.

TABLE 1

| Composition of the hydrogenation products | |
|---|---|
| $H_2O$ | 26.5% |
| THF | 36.45% |
| Propanol | 0.72% |
| Butanol | 1.53% |
| Butyrolactone | 13.63% |
| Butanediol | 17.91% |
| Remainder | 3.36% |

TABLE 2

| Product distribution after acid treatment | |
|---|---|
| $H_2O$ | 30.30% |
| THF | 52.5% |
| Propanol | 0.75% |
| Butanol | 1.68% |
| Butyrolactone | 14.46% |
| Butanediol | — |
| Remainder | 0.31% |

Example 2

The hydrogenation products used in Example 1 were treated with 0.2% by weight of bentonite K10 and treated by a method similar to that of Example 1 for several hours at 185° C. and worked up. Virtually the same results were achieved as in Example 1.

Example 3

The hydrogenation products used in Example 1 were reacted with 0.2% by weight of concentrated phosphoric acid in an autoclave under autogenous pressure at 260° C. The butanediol dehydrated completely to give THF.

Example 4

The hydrogenation products used in Example 1 were treated with 0.2% by weight of the cation exchanger Lewatit® SPC 118, in its H® form, at from 118 to 140° C. by a method similar to that of Example 1, and the mixture was worked up. The conversion was complete. Acid treatment of the hydrogenation products gave more THF than would have been expected from the BD content of the hydrogenation products. This is presumably attributable to the acid-catalyzed decomposition of byproducts present in the hydrogenation products. GBL was obtained in the expected amount.

Example 5

The hydrogenation products used in Example 1 were reacted with 0.2% by weight of solid tungstophosphoric acid at 150° C. by methods similar to that of Example 1, and the mixture was worked up. THF and GBL were obtained in virtually quantitative yields. The conversion was complete.

Example 6

A typical, virtually GBL-free hydrogenation mixture having the composition

| Water | 28.9% by weight |
| --- | --- |
| THF | 35.8% by weight |
| BD | 29.3% by weight |
| Propanol | 0.9% by weight |
| Butanol | 1.7% by weight |
| GBL | 0.1% by weight |
| Remainder | 3.3% by weight | was treated with sulfuric acid by a method similar to that of Example 1 and worked up. The product distribution after the acid treatment was as follows:

| Water | 34.98% by weight |
| --- | --- |
| THF | 61.94% by weight |
| BD | — |
| Propanol | 0.9% by weight |
| Butanol | 1.76% by weight |
| GBL | 0.1% by weight |
| Remainder | 0.29% by weight |

Example 7 (Comparative Example)

The products from the hydrogenation of MAA, having the composition as shown in Table 1, were separated into the products THF, GBL and BD by distillation using the method of U.S. Pat. No. 4,751,334.

To this end, THF and water were distilled off in a first column, and the THF/water azeotrope was worked up to give pure THF in accordance with U.S. Pat. No. 4,912,236. Water, propanol, butanol, GBL, BD and the medium-boiling and high-boiling components were produced at the bottom of the first column. The water and the organic byproducts were distilled off at the head of the second column. The bottom product in the second column was passed to the third column, the GBL first cut column, and subsequently to the fourth column, the pure GBL column. The GBL obtained in this column had a purity of about 98%. The principal impurity was butoxybutanol, making up about 1%.

The bottom product from the fourth column was distilled in a fifth column to remove the first cut of BD and in a sixth column to give pure BD. Under these conditions, BD was obtained in a purity of about 96% and was contaminated principally by GBL which had formed in the bottom of the sixth column due to thermal decomposition of high-boiling components. This contamination was avoided by prior separation of BD/high-boiling components in a further column. The BD obtained in this way was suitable for cyclization to give THF in a known manner.

We claim:

1. In a process for the preparation of tetrahydrofuran or tetrahydrofuran and γ-butyrolactone from the crude product which is obtained by the hydrogenation of a compound selected from the group consisting of maleic acid, succinic acid, maleic anhydride, succinic anhydride and fumaric acid, and which contains 1,4-butanediol as the main impurity, the improvement which comprises:
   treating the crude hydrogenation product, directly and without prior work-up to remove impurities, at from 100 to 300° C. with a non-oxidizing protic acid selected from the group consisting of mineral acids, solid protic acids capable of acting as Brönstedt acids and acidic organic cation exchangers, until the 1,4-butanediol is substantially completely cyclized to tetrahydrofuran, and
   isolating tetrahydrofuran and γ-butyrolactone from the reaction mixture by distillation.

2. An improved process as claimed in claim 1, wherein the non-oxidizing protic acid is a mineral acid selected from the group consisting of sulfuric acid and phosphoric acid.

3. An improved process as claimed in claim 2, wherein the non-oxidizing protic acid is sulfuric acid.

4. An improved process as claimed in claim 1, wherein the non-oxidizing protic acid is a phyllosilicate.

5. An improved process as claimed in claim 4, wherein the non-oxidizing protic acid is a bentonite.

6. An improved process as claimed in claim 1, wherein the non-oxidizing protic acid is an organic cation exchanger.

7. A process as claimed in claim 1, wherein the non-oxidizing protic acid is added to the crude hydrogenation product in an amount of from 0.01 to 10% by weight, with reference to the hydrogenation products.

8. A process as claimed in claim 7, wherein the amount of acid added is from 0.01 to 5% by weight.

9. A process as claimed in claim 7, wherein the amount of acid added is from 0.1 to 1% by weight.

10. A process as claimed in claim 7, wherein the added acid is sulfuric acid.

* * * * *